(12) United States Patent
Hecker et al.

(10) Patent No.: US 6,299,603 B1
(45) Date of Patent: Oct. 9, 2001

(54) INJECTION APPARATUS AND METHOD OF USING SAME

(76) Inventors: Karl I. Hecker, 400 Hurricane Rd., Keene, NH (US) 03431-2161; Leslie A. Clark, 829 #B Lincoln Ave., Alameda, CA (US) 94501; James F. Pfeiffer, 2369 Thackery Ave., Oakland, CA (US) 94611; Lyle M. Bowman, 5135 Mount Tam Cricle, Pleasanton, CA (US) 94588

(*) Notice: Subject to any disclaimer, the term of this patent is extended or adjusted under 35 U.S.C. 154(b) by 0 days.

(21) Appl. No.: 09/366,703

(22) Filed: Aug. 2, 1999

Related U.S. Application Data

(63) Continuation-in-part of application No. 09/127,919, filed on Aug. 3, 1998.

(51) Int. Cl.⁷ .................................................. A61M 5/00
(52) U.S. Cl. ........................ 604/181; 604/506; 604/289; 606/166
(58) Field of Search ..................................... 604/116, 117, 604/164, 174, 177, 180, 48, 264, 272, 274, 506–510, 289; 606/166

(56) References Cited

U.S. PATENT DOCUMENTS

| | | |
|---|---|---|
| 2,033,397 | 3/1936 | Richman . |
| 2,591,457 * | 4/1952 | Maynes ................................ 604/137 |
| 2,760,483 | 8/1956 | Tassicker . |
| 3,626,940 | 12/1971 | Zaffaroni . |
| 3,890,970 | 6/1975 | Gullen . |
| 3,961,628 | 6/1976 | Arnold . |
| 4,186,448 | 2/1980 | Brekke . |
| 4,454,151 | 6/1984 | Waterbury . |
| 4,499,898 | 2/1985 | Knepshield et al. . |
| 4,534,348 | 8/1985 | Fedorov et al. . |
| 4,549,529 | 10/1985 | White . |
| 4,552,146 | 11/1985 | Jensen et al. . |
| 4,578,061 * | 3/1986 | Lemelson ........................ 604/170.01 |
| 4,580,561 | 4/1986 | Williamson . |
| 4,688,570 | 8/1987 | Kramer et al. . |
| 4,759,746 | 7/1988 | Straus . |
| 4,853,224 | 8/1989 | Wong . |

(List continued on next page.)

FOREIGN PATENT DOCUMENTS

| | | |
|---|---|---|
| WO 92/19296 | 11/1992 | (WO) . |
| WO 95/32756 | 12/1995 | (WO) . |

OTHER PUBLICATIONS

Verbeek, A.M., et al., "Recurrent intrascleral cyst after strabismus surgery," *Graef's Arch Clin Exp Ophthalmol*, 234:S 229–S 231 (1996). (Abstract previously submitted).

Primary Examiner—Richard K. Seidel
Assistant Examiner—Jennifer Maynard
(74) Attorney, Agent, or Firm—Arnold & Porter

(57) ABSTRACT

The present invention relates to an apparatus and method for using the apparatus for injecting an agent into a tissue, particularly into thin tissues such as the sclera of the eye. The invention provides an apparatus and method for effectively imbedding a needle into a tissue at a predetermined penetration approach angle and penetration distance thereby reducing the risk of penetrating the full thickness of the tissue. The invention includes a support element and a needle guide platform disposed on the support element with an external support surface and a channel extending therethrough and terminating in an aperture at the support surface. A needle disposed in the channel is axially movable along an axis of injection through the channel. The needle is movable from a first retracted position to an extended position corresponding to the penetration distance, along the axis of injection. The axis of injection forms a penetration approach angle of up to about 60° with a tangent of the support surface at a point of intersection of the axis of injection with the projection of the support surface across the aperture.

8 Claims, 13 Drawing Sheets

U.S. PATENT DOCUMENTS

| | | |
|---|---|---|
| 4,863,457 | 9/1989 | Lee . |
| 4,957,117 | 9/1990 | Wysham . |
| 4,968,296 | 11/1990 | Ritch et al. . |
| 4,990,135 | 2/1991 | Truesdale . |
| 4,997,652 | 3/1991 | Wong . |
| 5,049,142 | 9/1991 | Herrick et al. . |
| 5,152,769 | 10/1992 | Baber . |
| 5,164,188 | 11/1992 | Wong . |
| 5,167,641 | 12/1992 | Schmitz . |
| 5,207,660 | 5/1993 | Lincoff . |
| 5,273,530 | 12/1993 | del Cerro et al. . |
| 5,279,565 | 1/1994 | Klein et al. . |
| 5,284,476 | 2/1994 | Koch . |
| 5,294,604 | 3/1994 | Nussenblatt et al. . |
| 5,314,419 | 5/1994 | Pelling . |
| 5,336,178 | 8/1994 | Kaplan et al. . |
| 5,342,377 | 8/1994 | Lazerson . |
| 5,370,607 | 12/1994 | Memmen . |
| 5,391,174 | 2/1995 | Wetson . |
| 5,409,457 | 4/1995 | del Cerro et al. . |
| 5,419,777 | 5/1995 | Hofling . |
| 5,437,640 * | 8/1995 | Schwab .................................. 604/116 |
| 5,443,505 | 8/1995 | Wong et al. . |
| 5,454,796 | 10/1995 | Krupin . |
| 5,496,329 | 3/1996 | Reisinger . |
| 5,499,991 | 3/1996 | Garman et al. . |
| 5,538,504 | 7/1996 | Linden et al. . |
| 5,562,691 | 10/1996 | Tano et al. . |
| 5,562,693 | 8/1996 | Devlin et al. . |
| 5,609,574 | 3/1997 | Kaplan et al. . |
| 5,630,827 | 5/1997 | Vijfvinkel . |
| 5,632,984 | 5/1997 | Wong et al. . |
| 5,643,292 | 7/1997 | Hart . |
| 5,674,240 | 10/1997 | Bonutti et al. . |
| 5,702,414 | 12/1997 | Richter et al. . |
| 5,707,643 | 1/1998 | Ogura et al. . |
| 5,713,860 | 2/1998 | Kaplan et al. . |
| 5,746,716 | 5/1998 | Vigil et al. . |
| 5,767,079 | 6/1998 | Glaser et al. . |
| 5,770,589 | 6/1998 | Billson et al. . |
| 5,911,707 * | 6/1999 | Wolvek et al. ....................... 604/116 |

* cited by examiner

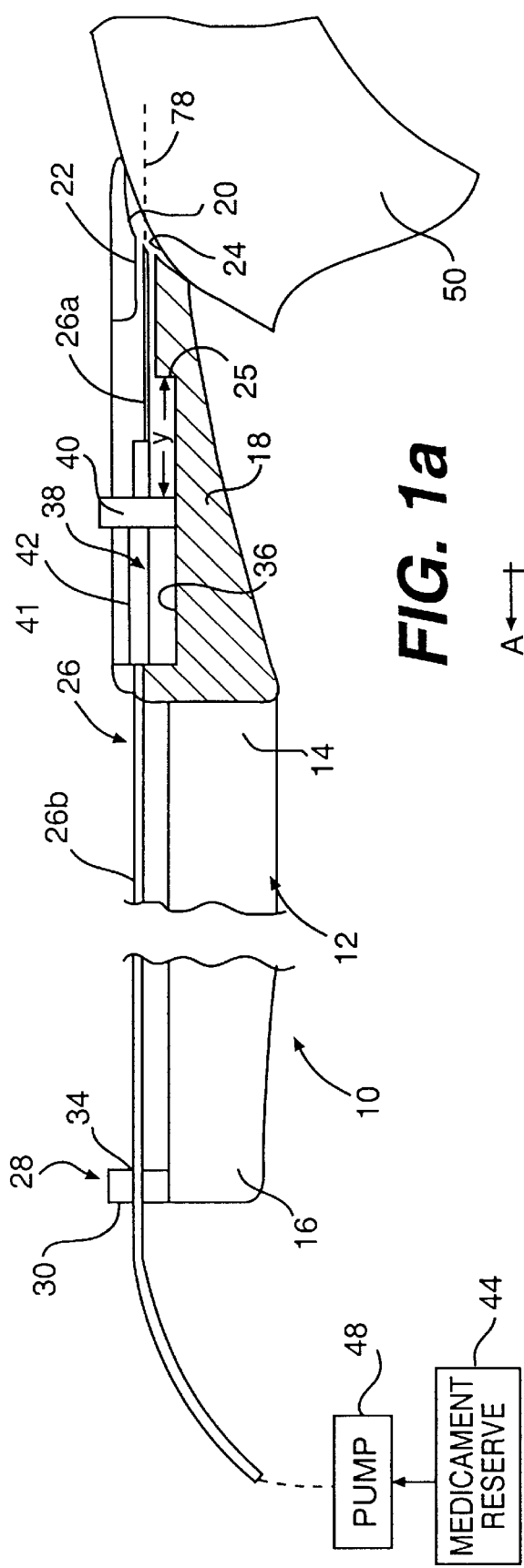
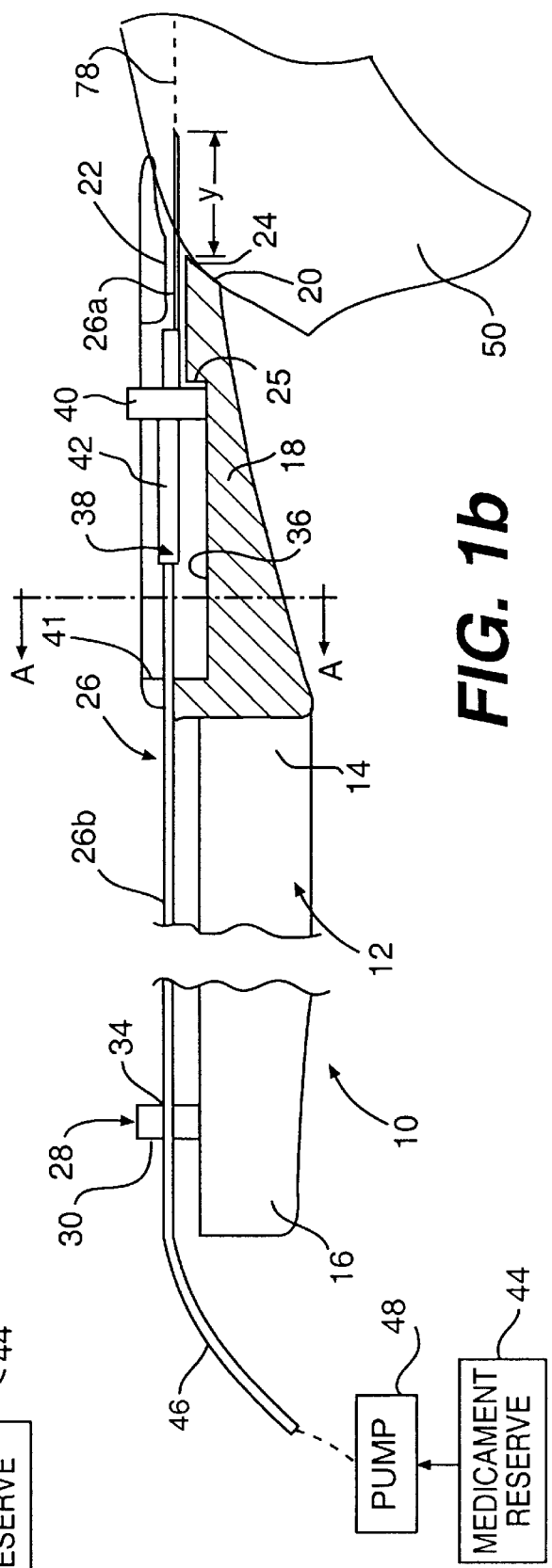

INJECTION APPARATUS AND METHOD OF USING SAME

The present application is a continuation-in-part of application Ser. No. 09/127,919, filed Aug. 3, 1998, the entirety of which is herein incorporated by reference.

FIELD OF THE INVENTION

The present invention is directed to a method and apparatus for injecting an agent into a tissue and, more particularly, to a method and apparatus for injecting an agent into a thin tissue such as the sclera of the eye.

BACKGROUND

There are two basic mechanisms for delivering exogenous agents, such as drugs and diagnostics, to certain types of body tissues. The most common is delivery via systemic administration.

In systemic administration, the agent is introduced into the systemic, or general, circulation by ingestion, injection, or inhalation. Circulating blood delivers the agent to the target tissue by either passive or active transport. The advantage to this method is that systemic administration, especially by ingestion, is simple. A disadvantage, however, is that the drug or medicament must be delivered at relatively high dosages in order to reach the targeted area in sufficient quantity. Moreover, the agent is delivered to the entire body, which can include sites where the agent may cause significant side effects. This is especially true for chemotherapeutic agents that tend to be toxic.

Another significant disadvantage is that certain tissues, such as brain or eye tissue, do not allow some types of chemicals to transfer well from the blood.

An alternative to systemic administration is to deliver the drug to the tissue by placing it directly into the tissue or in close proximity thereto. In order to deliver an agent directly to a specific tissue, there must first be a suitable deposit site. Preferably, this deposit site will be in close proximity to the targeted area.

A general example of this type of direct delivery method, is the injection of an agent to a site of pain, such as a muscle of the leg or arm or a particular joint. A more specific example of this type of direct delivery method is the introduction of slow release, drug-containing biocompatible particle implants directly into the anterior and/or posterior portions of the eye. Generally, these implants have been delivered into the vitreous humor of the eye via an intravitreal injection. While this is an effective method for delivering the agent to the targeted area with a reduced systemic loading, it carries a significant risk of damage to the tissues in the posterior portion of the eye. Furthermore, patient compliance for chronic administration is problematic due to the associated discomfort.

Another conventional example of this type of delivery to the eye is eyedrops delivered to the eye. Eyedrops act to deliver drugs directly to the anterior part of the eye by instillation into the cul de sac. The drugs are then moved from the tears of the eye across the cornea and into the anterior chamber without first entering the systemic circulation path. The advantage of this mode of delivery is that the drug is concentrated in the target tissue with a much lower systemic loading. This tends to reduce the above-mentioned systemic effects. The disadvantage of this type of administration is that not all tissues are accessible by this route of administration and tears may also remove a significant portion of the drug away from the targeted area relatively quickly.

Regardless of the method of delivery, drugs and other exogenous chemicals are cleared from any site of injection by a combination of mechanisms. Among these are: enzymatic degradation; diffusion into the surrounding tissue; and transport by the systemic circulation. Of these, transport by the systemic circulation is usually the most predominant mechanism. Accordingly, the deposit site should have a relatively low rate of clearance into the systemic circulation in order to reduce the systemic loading.

Many biological tissues, such as some layers of the walls of blood vessels and fallopian tubes, as well as the sclera of the eye, have relatively few cells and blood vessels and tend to exhibit properties which make them desirable deposit sites. These types of tissues are composed of intertwined fibers and fluid. As such, they are considered porous media in that the areas between the fibers form a continuous network of "channels" (interstitial space). These tissues also exhibit relatively low overall drug clearance rates because there is little or no enzymatic activity or blood flow, which leaves diffusion as the major elimination mechanism.

Thus, drugs deposited into these types of tissues will usually remain localized to the site of injection longer than in more cellular and vascularized tissues, such as the skin. The problem with these tissues, however, is that most of them are thin (e.g., from about 0.3 mm up to about 1.5 mm) and present numerous obstacles to injection within the thin tissue.

Generally, when an exogenous fluid is injected into a porous tissue, such as the sclera of the eye, the fluid must displace the endogenous fluid in the channel or interstitial space in the tissue. The rate at which exogenous fluid may be introduced into the tissue is inversely propositional to the resistance caused by the channels. In addition, when a needle is placed into a tissue, it creates a fluid path to the exterior of the tissue along the outer surface of the needle.

When making an injection, one consideration is the minimization of the leakage of fluid along this path to the exterior. In considering this leakage, it has been found that the resistance to fluid flow along the needle path is directly proportional to the length of the needle that is in contact with the tissue (i.e., length of the needle imbedded in the tissue). In considering the leakage, it has further been found that the ratio of the flow rate along the needle to the flow rate through the tissue is inversely proportional to the ratio of the respective resistances. Thus, it would be beneficial to increase the resistance to flow along the needle by increasing the penetration distance of the needle into the tissue. However, because of the inaccuracies and inherent variability with human intervention in controlling the penetration distance of the needle during such injections, control over the penetration distance of the needle, especially in thin tissues, presents numerous obstacles.

In drug delivery to the retinal or chordal region of the eye, numerous problems may be encountered. For example, with direct injection, choroidal hemorrhaging leading to retinal detachment may occur. In addition, with systemic administration, side effects and molecular size present problems that must be accommodated. Further, topical application to the cul de sac presents transport difficulties.

In addition, delivery of large molecules or particles (referred to herein as "large agents"), such as anti-bodies, viral vectors and the like, to the back of the eye (retina and choroid) is very difficult unless an injection is made directly into the vitreous humor of the eye. An alternative to such a method is to pierce the sclera at the back of the eye and make an injection directly to the retinal or choroidal tissues. As noted above, such procedures have substantial risk in causing damage to the ocular tissues. Moreover, delivery of these types of agents from a remote depot, such as the sclera or subconjunctival space is problematic because the agents tend to disperse very slowly from the site of injection.

Various approaches have been proposed to overcome the problems of injecting drugs or other therapeutic agents into the retina or choroidal regions. Generally, drugs have been delivered to the retina via the vitreous humor via an intravitreal injection. As noted above, while the method may be an effective method, it carries a significant risk of retinal detachment and/or infection. Furthermore, patient compliance for chronic administration is problematic due to the associated discomfort. Therefore, an alternate method of delivery is desirable, especially for the chronic delivery of either large molecules, such as proteins, anti-bodies, viral vectors, or drugs that have a high systemic toxicity.

A proposed method for delivering and withdrawing a sample to and from the retina is shown in U.S. Pat. Nos. 5,273,530 and 5,409,457. This device is for delivering a sample directly to the retina or subretinal region or withdrawing a sample therefrom. Although the device discloses a collar for regulating the depth the tip penetrates into the intraocular or subretinal region, the collar and tip are not adapted to prevent the penetration of the full thickness of the sclera and the choroid tissues in delivering the samples to the retina. Indeed, the device requires that the sclera and choroid be traversed by the tip prior to delivering or withdrawing the sample from the retina or subretinal region. Penetration into the choroid and retina can cause hemorrhage and possible retinal detachment. Moreover, the user must manipulate the tip, or needle through the ocular layers. Such imprecise movement could cause potential complications during the traversal of the ocular layers. Further, the device does not overcome the inaccuracies and variability which are inherent in injecting into a tissue wherein the path of the needle and movement of the needle is controlled by human intervention. Indeed, such inaccuracies may result in piercing the entire thickness of the thin layer tissue resulting in complications or may present drug delivery problems as described below.

Injections into thin tissues, such as the sclera of the eye or the walls of blood vessels, present problems for such a device. The penetration distance of the needle into the tissue is limited by the thickness of the tissue, the orthogonal approach of the needle to the tissue surface, and human control of the needle. Indeed, it is difficult for the user to control the angle and penetration distance of the needle in a free-handed manner, specifically into thin layer tissues.

For example, the sclera of the human eye generally varies from a thickness of about 0.3 mm to about 1.5 mm. Thus, injections made with a needle that is in a generally orthogonal relationship to the surface of the tissue are likely to fail due to fluid leakage from the site of injection or piercing the entire thin tissue thereby causing complications to underlying tissues or releasing the agent away from the targeted location.

In the case of scleral injection, the close proximity of the sclera to the retina means that a significant fraction of any agent injected into the intrascleral space may reach the retina by passive diffusion. There may be little direct elimination of any agent by either enzymatic degradation, clearance into the blood stream, or removal by tears due to the acellular and nonvascular nature of the sclera. Moreover, complications due to damaging the underlying choroid and retinal layers may be eliminated.

Another area which could benefit from direct injection is the wall of blood vessels especially those with atherosclerotic plaques. While access to the outer surface of many vessels is difficult, access to the inner surface of the vessel is not, there being a number of devices available for that purpose. However, delivery of therapeutic agents directly to these sites is problematic because the high rate of blood flow within the vessel tends to prevent exogenous agents from adhering to the inner surface. Systemic administration, while possible, is problematic because the region of tissue that would benefit from the therapeutic agent is small in relationship to overall size of the vasculature. Thus, the agent must be administered in great excess in order to achieve therapeutic efficacy.

The walls of certain blood vessels, especially those of the heart, are generally less than 1 mm thick. Precise placement within the wall is difficult. Insertion of a needle into the vessel wall can perforate the vessel causing hemorrhage into the surrounding tissue. In the vessels of the heart, such a perforation can be life threatening.

Devices for direct administration of fluids to the vasculature are known in the prior art. These rely on substantially orthogonal approaches to the inner wall of the vessel, the disadvantages of which have already been discussed above. In addition, these devices rely on an external reservoir for the medicament. A better method of injection where the needle is inserted farther into the tissue should reduce the amount of medicament that leaks from the site of injection. Furthermore, a device with a medicament reservoir deployed closer to the needle would require substantially smaller volumes of fluid and therefore less waste.

Thus, as set forth above, there is a need for an apparatus and method that reliably and safely facilitates injecting into a thin tissue, for example, the sclera, a therapeutic agent which is delivered either directly or allowed to diffuse to the targeted area, for example, the retina. There is a further need for a device that is effective for imbedding a needle in a guided injection at a predetermined penetration approach angle and penetration distance within the tissue such that a hydrodynamic seal between the tissue and the needle limits injected fluids from being expelled from the tissue due to the force of the injection. Furthermore, there is a need for a method for imbedding the needle at a penetration distance of greater than at least the thickness of the tissue without penetrating the full thickness of the tissue layer which could cause damage to underlying tissues. Moreover, there is a need for a safe and effective method and apparatus for delivering large molecules or particles, or large agents, such as anti-bodies, viral vectors, and the like, to the back of the eye, for example, the retina and choroid.

SUMMARY OF THE INVENTION

Accordingly, the present invention is directed to injection apparatuses and methods for injecting agents into tissues and, more specifically, for injecting agents into thin tissues such as the sclera of the eye that substantially obviates one or more of the problems due to the limitations and disadvantages of the related art.

One objective of the present invention is to provide a method and apparatus that inserts a needle into the tissue such that the needle travels into the tissue substantially parallel to the tissue surface. This increases the length of the needle that can be imbedded into the tissue. This, in turn, increases the resistance to flow along the imbedded needle and decreases leakage from the site of injection. This allows for greater volumes of fluid to be injected and also allows for variance in human control.

The invention provides an apparatus and method that reliably and safely facilitates injecting a therapeutic agent into a thin tissue, such as the sclera of the human eye, which then is allowed to diffuse to the targeted area, for example, the retina. The invention also provides an apparatus and method for effectively imbedding a needle into a tissue in a guided injection at a predetermined penetration approach angle and penetration distance sufficient to provide a hydrodynamic seal between the tissue and the needle such as to minimize injected fluids from being expelled from the tissue due to the force of the injection. Furthermore, the invention provides an improved method for imbedding the needle in such a manner that reduces the risk of penetrating the full thickness of the tissue which could cause damage to underlying tissues. The invention also reduces the inaccuracies and variability, which are inherent in human-controlled movements of injection apparatuses.

Additional features and advantages of the invention will be set forth in the description which follows, and in part will be apparent from the description, or may be learned by practice of the invention. The objectives and other advantages of the invention will be realized and attained by the apparatuses and methods particularly pointed out in the written description and claims hereof as well as the appended drawings.

The present invention relates to an apparatus for delivering an agent into a tissue. The apparatus includes a support element and a needle guide platform disposed on the support element. The needle guide platform has an external support surface and a channel extending therethrough. The channel terminates in an aperture at the support surface. The apparatus further includes a needle having a first end and a second end. The needle includes a sidewall defining an outlet in said needle and an inlet disposed in the needle. The outlet may be defined in the sidewall itself or at the end of the needle. Preferably, the outlet is at the end of the needle for direct injection and at the sidewall for "indirect" injection (as defined below). The inlet is preferably in fluid flow communication with the outlet.

In another aspect, the present invention relates to a method for injection. The method comprises placing a needle into a tissue, wherein the tissue preferably has a first surface and a second surface defining a tissue thickness. The needle is placed into the tissue at a penetration distance of greater than about the tissue thickness but such that even if extended the needle could not intersect the second tissue surface. The method further includes inserting an agent into the tissue through an outlet defined by a sidewall of the needle. The agent is inserted into the tissue through the outlet such that the agent exiting the outlet is in an orientation towards one of the first and second surface of the tissue in said needle when the needle is placed into the tissue.

In another aspect, the present invention relates to a method for injecting an agent into a target tissue. The target tissue has a first surface and a second surface defining a tissue thickness. The method preferably includes disposing a needle in an injection apparatus. The apparatus preferably includes a support element and a needle guide platform disposed on the support element. The apparatus further includes an external support surface and a channel extending therethrough. A needle is preferably disposed in the channel and movable along an axis of injection through the channel. The needle preferably has a first end and a second end and includes a sidewall defining an outlet in the needle and an inlet disposed in the needle. The inlet is preferably in fluid flow communication with the outlet.

The method further includes placing the needle in fluid flow communication with a medicament reservoir. In addition, the method includes positioning the injection apparatus adjacent a tissue surface, advancing the needle outwardly through the channel, and imbedding the needle into the target tissue such that the outlet is adjacent to, and oriented in a direction substantially facing, one of the first and second surface of the tissue. The method further includes transferring the agent into the tissue.

In another aspect, the present invention relates to an apparatus for injecting an agent into a tissue. The apparatus includes a support element having a distal end and a proximal end. The apparatus further includes a needle guide platform disposed on the distal end of the support element. The needle guide platform preferably has an external support surface and a channel extending therethrough, the channel preferably terminates in an aperture at the support surface.

The apparatus also preferably includes a needle disposed in the channel. The needle being axially movable through the channel from a retracted position to an extended position. The needle has a first end and a second end. The needle also includes a sidewall defining an outlet in the needle and an inlet disposed in the needle. The inlet is in fluid flow communication with the outlet. The needle preferably extends from the aperture when moving from the retracted position to the extended position, whereby, an axis of injection of the needle forms an acute penetration approach angle of up to about 60° with a tangent of the support surface at a point of intersection of a longitudinal axis of the needle with a projection of the support surface across the aperture.

In another aspect, the present invention relates to an apparatus for injecting into a wall of a vessel. The invention includes a catheter body having a distal end, a proximal end, and an inflation passage. A needle guide platform is included and disposed on the distal end of the catheter body and has an external support surface and a channel extending therethrough. The channel terminates in an aperture at the support surface.

The invention further includes an expansion member disposed in the catheter body near the distal end. The expansion member is in fluid communication with the inflation passage.

In addition, the invention includes a needle disposed in the channel. The needle is axially movable along an axis of injection through the channel from a retracted position to an extended position. The needle has a front outlet and an inlet rearwardly located relative to the front outlet. The front outlet is in fluid flow communication with the inlet. The needle extends from the aperture when moving from the retracted position to the extended position. The needle guide platform may be disposed about the vessel by inflating the expansion member such that the needle is extendable from the aperture and into the wall of the vessel and further wherein, the needle moves along the axis of injection which forms a penetration approach angle of up to about 60° with a tangent of the support surface at a point of intersection of the axis of injection with a projection of the support surface across the aperture.

In another aspect, the present invention relates to a method for placing a needle in a tissue. The tissue has a first surface and a second surface, which define a tissue thickness. The needle is placed into the tissue from the first tissue surface at a penetration distance of greater than about the tissue thickness but such that even if extended the needle could not intersect the second tissue surface.

In another aspect, the present invention relates to a method for injecting an agent into a tissue at a point of injection, the tissue having a first surface and a second surface. The first surface and second surface define a tissue thickness. The invention includes the steps of disposing a needle in an injection apparatus, which includes a support element having a distal end and a proximal end. The apparatus further includes a needle guide platform disposed on the distal end of the support element. The needle guide platform has an external support surface and a channel extending therethrough. The channel terminates in an aperture at the support surface. The needle is disposed in the channel and movable along an axis of injection through the channel from a restricted position to an extended position. The needle has a front outlet and an inlet rearwardly located relative to the front outlet. The front outlet is in fluid flow communication with the inlet. The needle extends from the aperture when moving from the retracted position to the extended position. The apparatus further includes an actuator for advancing and retracting the needle through the channel.

The invention further includes placing the needle in fluid flow communication with a medicament reservoir and positioning the injection apparatus adjacent the tissue such that the support surface is in substantial contactual relationship with the tissue. The support surface is configured to substantially conform to the geometry of the first surface of the tissue. The invention further provides for advancing the needle outwardly through the aperture and imbedding the needle in the tissue. Finally, a medicament is transferred from the medicament reservoir through the needle and into the tissue.

As used herein, the phrase "indirect injection" relates generally to delivery of an agent to a targeted tissue, preferably via injection of the agent through a cannula, needle, or other suitable device into a second tissue that is near or in substantial contact with the targeted tissue.

It is to be understood that both the foregoing general description and the following detailed description are exemplary and explanatory and are intended to provide further explanation of the invention as claimed.

The accompanying drawings are included to provide a further understanding of the invention and are incorporated in and constitute a part of this specification, illustrate several embodiments of the invention and together with the description serve to explain the principles of the invention.

BRIEF DESCRIPTION OF THE DRAWINGS

The accompanying drawings, which are incorporated in and constitute a part of this specification, illustrate embodiments of the invention and, together with the description, serve to explain the features, advantages, and principles of the invention.

FIG. 1a is a sectional elevational view of an exemplary embodiment of the present invention shown with the needle in the retracted position;

FIG. 1b is a sectional elevational view of an exemplary embodiment of the present invention shown with the needle in the extended position;

DETAILED DESCRIPTION OF THE PREFERRED EMBODIMENTS

Reference will now be made in detail to the present preferred embodiments of the invention, examples of which are illustrated in the accompanying drawings. The exemplary embodiments of this invention are shown in some detail, although it will be apparent to those skilled in the relevant art that some features which are not relevant to the invention may not be shown for the sake of clarity.

Figure 1C:
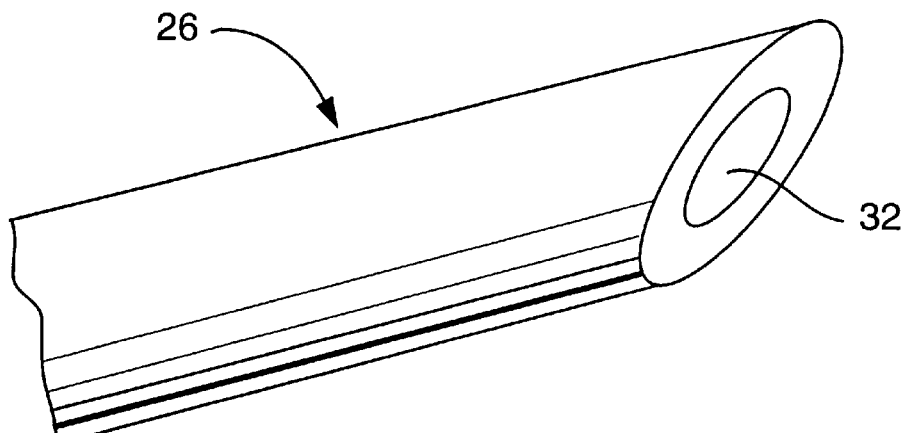
FIG. 1c is a detailed view of the front outlet of the needle of an exemplary embodiment of the present invention.

Referring to FIGS. 1a and 1b, there is illustrated, in a side-elevational sectional view, an exemplary apparatus of the present invention and is represented generally by reference numeral 10. The exemplary embodiment of the apparatus 10 and tissue 50 shown in FIGS. 1a–1d have been expanded in scale in order to provide clarity to the description of the invention and should not be construed to place limits on the dimensions or characteristics thereof. Moreover, the apparatus 10 and tissue 50 are shown in different scales for added clarity.

The apparatus 10 includes a support element 12 having a distal end 14 and a proximal end 16. Support element 12 allows a user to grasp and position the apparatus with one hand while manipulating the site of injection with the other hand. Alternatively, support element 12 may be placed in a retaining device or other well known support structure in order to provide increased stability throughout the injection process or to otherwise free up the hand of the user.

Support element 12 can be made of a metal such as stainless steel or aluminum, or may be made of other suitable materials. Alternatively, support element 12 can be made of plastic. The material from which support element 12 is made is preferably non-irritating to the particular targeted tissue. Support element 12 can be opaque or transparent, depending upon the particular application.

A needle guide platform 18 is disposed on the distal end 14 of support element 12. Preferably, the longitudinal axes of support element 12 and the needle guide platform 18 will be in a general parallel relationship, however, it should be apparent to one of ordinary skill in the art that the longitudinal axes may be coincidental, or at an angle to each other. This would depend upon the particular application for which the device may be directed.

The needle guide platform 18 has an external support surface 20 which is shaped to substantially conform to the surface of the tissue into which the injection is to be made, as will be described in more detail below. Needle guide platform 18 may be made of the same material as support element 12 or may be made of a different material if required. For example, support element 12 may be made of a light, transparent plastic, such as acrylic or other suitable plastic. Whereas needle guide platform 18 may be made of a material with a high coefficient of friction against the targeted injection tissue so that the device will not slip during use. Materials, such as, but not limited to, natural or synthetic rubber, may be suitable as would knurled or textured metals. Alternatively, needle guide platform 18 may be provided with a mechanism which is intended to impale the tissue, such as pointed projections 15 (one example of which is shown in FIGS. 1*e*), or to grip/pinch the tissue, such as a tapered groove 17 (shown in FIGS. 5*a*–5*c*), so as to hold the tissue 50 in a fixed relationship to the needle guide platform 18.

Figure 5A:
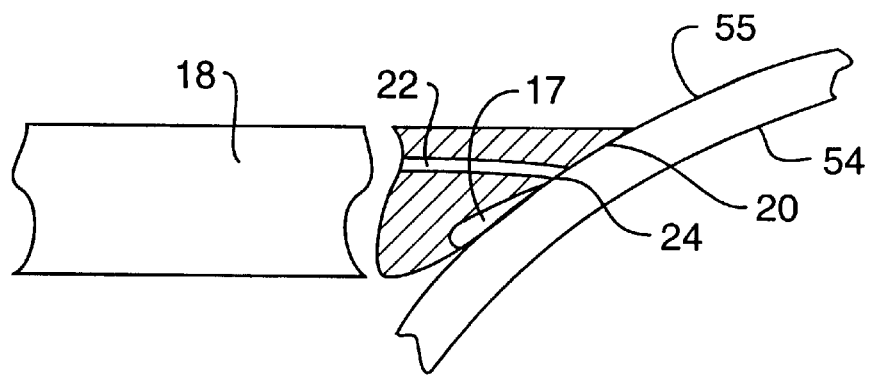
FIGS. 5a–5c illustrate an alternative embodiment for stabilizing the apparatus against the tissue.
Figure 5B:
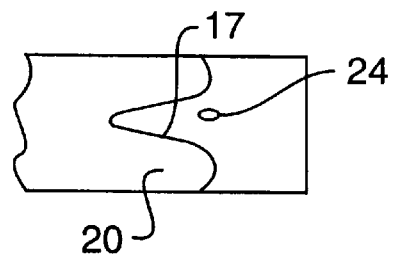
Figure 5C:
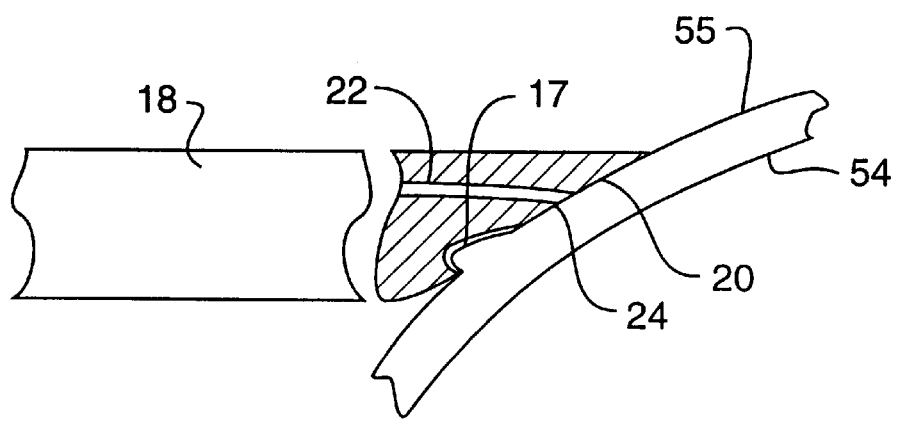

Referring to FIGS. 5*a*–5*c*, a tapered groove 17 is shown as part of the needle guide platform 18. The tapered groove 17 may allow for an overlying tissue, such as the conjunctiva 55 of the eye, to be gripped and/or pinched into the tapered groove 17 as the device is moved along the conjunctiva 55 and into position for injection into, for example, the sclera 54 of the eye. This is shown by way of example in FIGS. 5*a* and 5*c*. This may, as noted above, prevent the device from slipping during the subsequent injection.

A channel 22 extends along a longitudinal axis through the needle guide platform 18. Channel 22 terminates at the external support surface 20 in an aperture 24.

A needle 26 or other suitable cannula device is disposed in the needle guide platform 18. Preferably, needle 26 is disposed in channel 22 and is movable through channel 22 from a first retracted position to an extended second position along a longitudinal axis 78 of the needle 26. The longitudinal axis 78 preferably coincides with the longitudinal axis of the channel 22. It should be clear to one of ordinary skill in the art, however, that the longitudinal axis 78 might alternately be positioned such that it is not coincidental to the longitudinal axis of channel 22.

Needle 26 may be advanced from the first retracted position to the extended second position by a manual actuator 28 which is axially movably disposed on support element 12 and attached to the needle 26. Actuator 28 may rest in a groove (not shown) in support element 12 or may be attached for axial movement in any well known manner.

Actuator 28 may include a handle 30 connected at a rear extremity of actuator 28 for receiving an external actuating force directly from an operator of the apparatus 10. Other mechanisms such as a compressed gas/piston arrangement or a compression spring mounted to support element 12 may be used to provide the external actuating force to the needle 26. These mechanisms may likewise be externally triggered by the operator.

Needle 26 preferably comprises a first needle section 26*a* and a second cannula section 26*b*. Second section 26*b* may be either rigid, flexible, or a combination of the two. Alternatively, needle 26 may comprise a single needle section having a constant diameter. First section 26*a* is, however, preferably of a larger gauge (and thus of a smaller diameter) than second section 26*b*. For example, first section 26*a* may be 33 or 30 gauge and second section 26*b* may be 22 gauge. In general, it should be understood by one of ordinary skill in the art that first section 26*a* may be in the range of from about 26 gauge to 37 gauge, and second section 26*b* may be in the range of from about 12 gauge to about 22 gauge. It should be understood, however, that other needles of different gauge size may be suitable, depending on the particular tissue, patient and procedure, or depending on the physician's preference and needs. Generally, the diameter of the needle 26 will be less than the thickness of the targeted tissue 50. Sections 26*a* and 26*b* may be joined by any well known method, for example, but not limited to, soldering or welding. Alternatively, sections 26*a* and 26*b* may be joined by a threaded connection or a detachable fitting such as a separate threaded connector.

In order to deliver, or inject, agents into the tissue 50, needle 26 is hollow and has a front outlet 32 (shown in FIGS. 1*c*) in fluid flow communication with an inlet 34 rearwardly located relative to front outlet 32. Generally, the lumen, or hollow space of the needle 26, must be large enough to permit flow of relatively viscous agents or fluids without undue force being applied. In the exemplary embodiment shown in FIGS. 1*a* and 1*b*, inlet 34 is located at the rear portion of second section 26*b* of needle 26. It should be understood that inlet 34 may be located at any location along needle 26, such as the side of needle 26. Furthermore, it is preferable to have the distance between inlet 34 and outlet 32 as short as practical so that fluid retention between the inlet 34 and outlet 32 may be kept to a minimum.

Figure 1D:
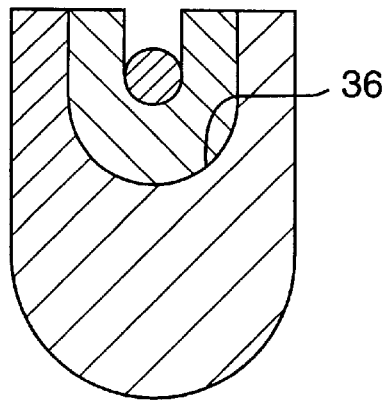
FIG. 1d is a cross-sectional elevational view of an exemplary embodiment of the present invention taken along line A—A of FIG. 1b.
Figure 1E:
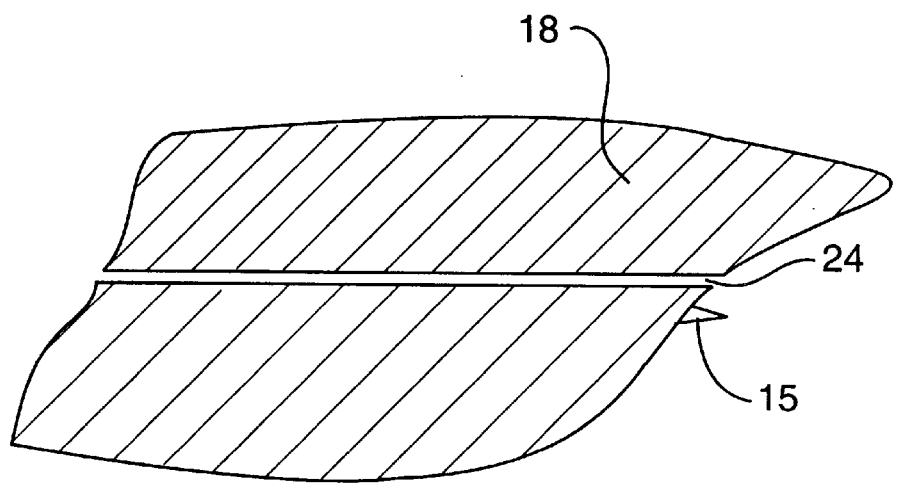
FIG. 1e is a partial view of an alternative embodiment for stabilizing the apparatus against the tissue.

As further shown in FIGS. 1*a*, 1*b*, and 1*d*, a groove 36 extends along an interior depressed rearward portion the needle guide platform 18. A flange member 38 having an outer flange portion 40 and a body portion 42 is axially movably disposed in groove 36. Flange member 38 is preferably rigidly connected to the needle 26 by any method well known in the art. Groove 36 may be semi-circular in shape as shown in FIG. 1*d* and flange member 38 may be circular in shape. However, it should be understood by one skilled in the art that other shapes may be used, for example, but not limited to, square or rectangular. Flange member 38 is configured to limit the distance needle 26 extends from support surface 20 through aperture 24 as will be described in more detail below. For example, flange member 38 may be attached to the needle 26 at a different location, however, this location must not permit the needle 26 to extend from the support surface 20 when the needle 26 is in the first retracted position.

A medicament reservoir 44 containing a therapeutic agent which is to be delivered, or injected, into tissue 50, is connected to the inlet 34 of needle 26 through a conduit 46. Conduit 46 may be any well known tubing or other mechanism for fluid transport. Preferably, conduit 46 will be flexible and will thereby provide full mobility to the operator. As shown in FIGS. 1*a* and 1*b*, preferably conduit 46 will be flexible tubing. Conduit 46 is in selective fluid flow communication with the hollow passage through needle 26 via inlet 34 to deliver the therapeutic agent to the front outlet 32 of needle 26 and thereafter into the targeted tissue 50. A predetermined amount of the therapeutic medicament or fluid may be delivered in response to, for example, the manual operation of a switch (not shown) to drive a pump 48, such as a syringe pump, which pumps into conduit 46 the desired amount of medicament or fluid. The medicament reservoir 44 supplies the medicament or fluid to pump 48.

Reference will now be made to the operation of the apparatus 10, specifically as shown in FIGS. 1*a* and 1*b*, in order to more clearly describe the interrelationship among the individual elements as well as the overall injection cycle. Referring first to FIGS. 1*a*, the apparatus 10 is shown generally in contactual relationship, via support surface 20, with a tissue 50 (enlarged in scale). If, however, one or more intervening layers of tissue separates the target tissue 50 from the apparatus 10, the apparatus 10 would be in general contactual relationship with the outer most layer of tissue. The needle 26 is in the retracted position (i.e., needle section 26*a* is not extending from the aperture 24 of support surface 20). The flange member 38 is disposed in the proximal end of the groove 36.

Once the apparatus 10 is placed in the desired location with regard to tissue 50, and specifically that the support surface 20 is in substantial contactual relationship with and stabilized against the tissue 50 (or an intervening layer of tissue), an operator may move or slide handle 30 of actuator 28 in the general axial distal direction along support element 12. This will cause the needle 26, as will be described immediately hereinafter, to be advanced from the retracted position of FIGS. 1*a* to an extended position as shown in FIGS. 1*b*.

Figure 1F:
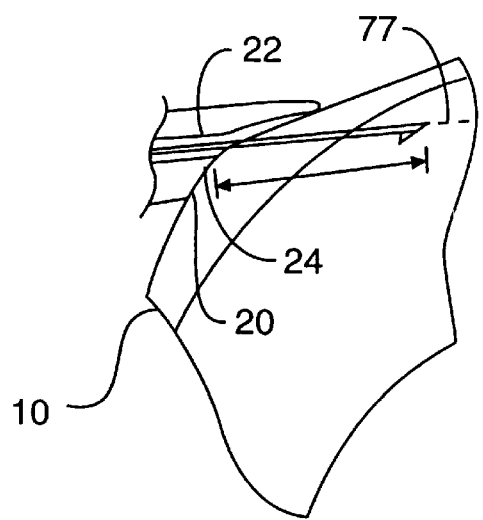
FIG. 1f is a detailed view of an exemplary embodiment of the present invention used with intervening layers of tissue.

As the handle 30 is moved by the user in the axial direction along support element 12, flange member 38 moves in the axial distal direction along the groove 36 which correspondingly moves the attached needle 26 in the axial direction along the channel 22 of needle guide platform 18. The forward or distal axial movement of the needle 26 and the flange member 38 continues until the forward face of the outer flange portion 40 contacts the raised portion 25 of groove 36. At this point the flange member 38 has moved a distance y (as shown in FIGS. 1*a*) and the needle 26 has extended forwardly from the aperture 24 of the support surface 20 and into the tissue 50 by a corresponding penetration distance y. As shown in FIG. 1*f*, if one or more layers of tissue separates the target tissue 50 from the apparatus 10, the corresponding penetration distance would be y minus the thickness of the intervening layer or layers of tissue 100 at the point of insertion x. It should be apparent that the penetration distance may be specifically chosen for various applications and corresponding changes to the attachment of flange member 38 onto needle 26 could be made to accommodate the targeted penetration distance.

As shown in FIGS. 1*b*, the forward face of the outer flange portion 40 of flange member 38 is in contact with the raised portion 25 of groove 36. Thus, forward axial movement of the needle 26 is impeded. The user may at this time separately engage a switch (not shown) to drive pump 48. Pump 48, in response to the switch, delivers the desired volume of fluid or medicament from the medicament reservoir 44 through the conduit 46, through the needle 26, and thereafter into the targeted site of injection within tissue 50.

Following injection of the fluid in the manner described above, the user may normally slide or move the handle 30 in the proximal axial direction along support element 12 which will in turn move the flange member 38 and the needle 26 in the corresponding direction. The user may continue to move the handle 30 in the proximal axial direction until the proximal end of the body portion 42 of the flange member 38 contacts the rearward wall 41 of channel 22. At this point and because of the particular dimensions for the elements, particularly the flange member 38, chosen for the specific application, the needle 26 will be safely retracted within the needle guide platform 18 and the apparatus 10 may be withdrawn away from the tissue 50 and/or any intervening layers of tissue. Alternatively, the user may pull the needle 26 directly out of the tissue 50.

Figure 2A:
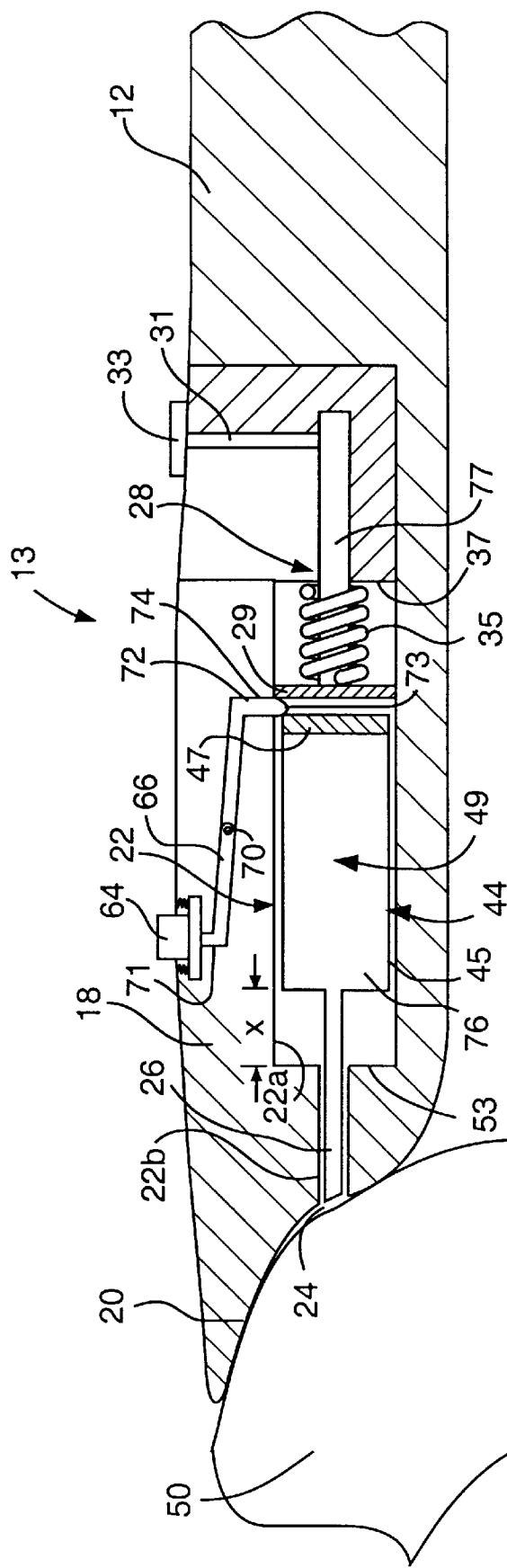
FIG. 2a is a sectional elevational view of a second exemplary embodiment of the present invention shown with the needle in the retracted position.
Figure 2B:
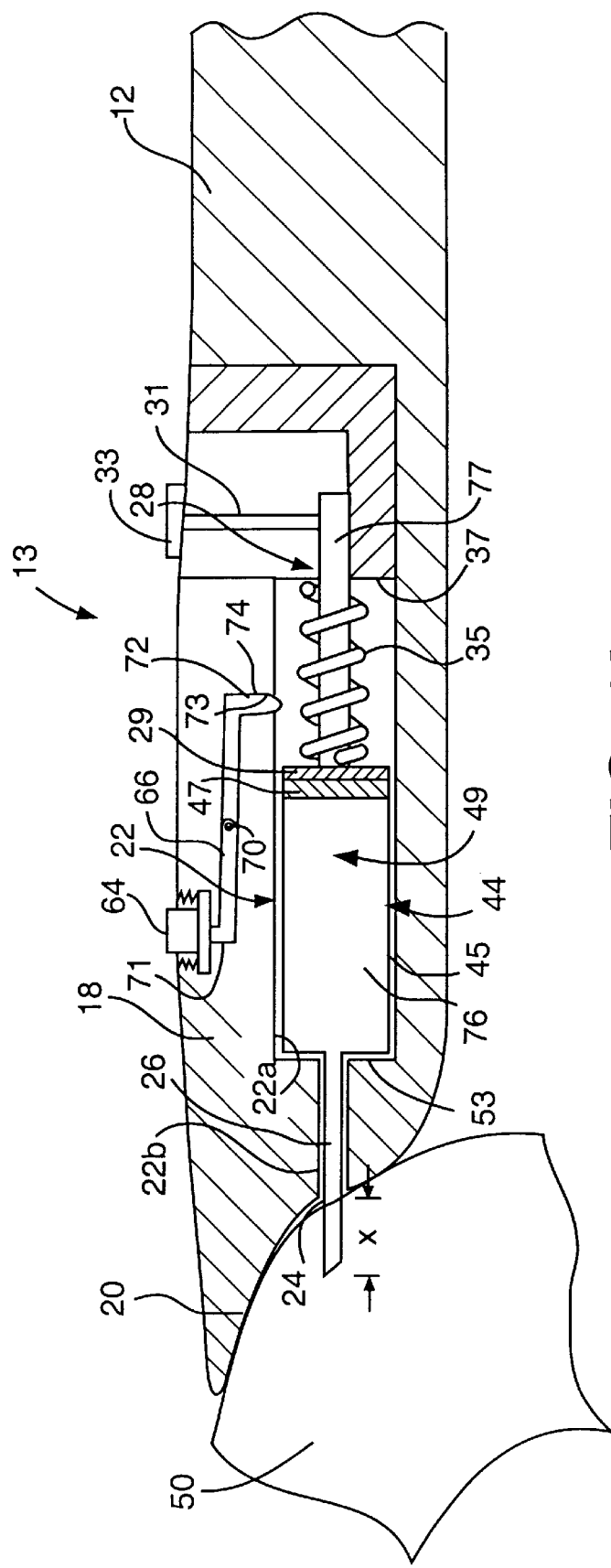
FIG. 2b is a sectional elevational view of a second exemplary embodiment of the present invention shown with the needle in the extended position prior to delivery of the fluid from the medicament reservoir.
Figure 2C:
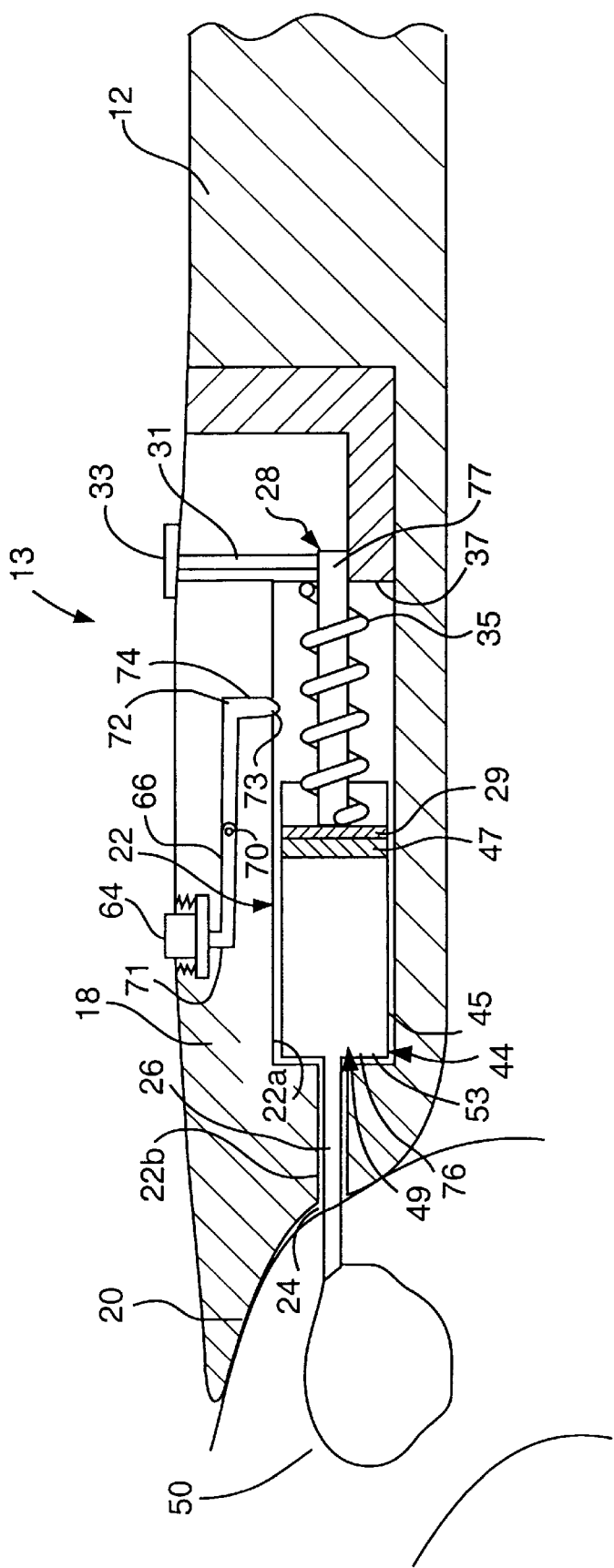
FIG. 2c is a sectional elevational view of a second exemplary embodiment of the present invention shown with the needle in the extended position after delivery of the fluid from the medicament reservoir.

Referring to FIGS. 2*a* through 2*c*, there is shown a second exemplary embodiment of the present invention. Corresponding reference numerals will be used where appropriate.

The second exemplary embodiment is represented generally by reference numeral 13. The exemplary embodiment of the apparatus 13 and tissue 50 shown in FIGS. 2*a*–2*c* have been expanded in order to provide clarity to the description of the invention and should not be construed to place limits on the dimensions or characteristics thereof. The second embodiment may also be used with intervening layers of tissue between the apparatus 13 and the target tissue 50. For clarity, the second embodiment will be explained without reference to intervening layers. One skilled in the art, however, will appreciate that the other embodiments may be used with multiple layers of tissue. Moreover, the apparatus 13 and tissue 50 are shown in different scales for added clarity.

Apparatus 13 has a support element 12 (shown in partial view) with a needle guide platform 18 disposed thereon. As noted above, preferably, the longitudinal axes of support element 12 and the needle guide platform 18 will be in a general parallel relationship, however, it should be apparent to one of ordinary skill in the art that the longitudinal axes may be coincidental, or at an angle to each other. This would depend upon the particular application for which the device may be directed.

Needle guide platform 18 includes an external support surface 20 that is shaped to substantially conform to the surface of the tissue 50 into which the injection is made. Needle guide platform 18 further includes a guide channel 22 disposed therein. Channel 22 preferably includes a proximal section 22*a* and a distal section 22*b*. Distal section 22*b* is preferably of smaller cross-sectional area than proximal section 22*a* and terminates at the external support surface 20 in an aperture 24. Proximal section 22*a* and distal section 22*b* may be of any practical shape and/or cross-section, however, each section is preferably cylindrical in shape and therefore circular in cross section.

A medicament reservoir 44 is axially movably disposed in the distal section 22*b* of channel 22. Preferably, medicament reservoir 44 is cylindrical in shape, however, any other well-known and practical shape may be used, for example, but not limited to, square or triangular. The medicament reservoir 44 has a housing or body 45 and a piston 47 sealingly axially movable therein for defining a variable volume chamber 49. Piston 47 may be formed of a suitable elastomer or other suitable material for sealing contact with the body 45 of the medicament reservoir 44. A tubular needle 26 is attached at its proximal end to the medicament reservoir 44 and is in fluid flow communication therewith.

An actuator 28 is axially movably disposed, in part, in the channel 22 of the needle guide platform 18 and extends through the proximal end thereof and, in part, in the support element 12, as shown in FIGS. 2a–2c. In the exemplary embodiment shown in FIGS. 2a–2c, actuator 28 includes a rod or shaft 77 having a plunger 29 disposed on the distal end of shaft 77 and an extension arm 31 disposed on the proximal end of shaft 77. A helical compression spring 35 is disposed on the portion of shaft 77 which is disposed in channel 22 of needle guide platform 18 and is interposed between the plunger 29 and the rearward wall 37 of channel 22. Extension arm 31 preferably extends generally perpendicular from shaft 77 to the exterior of support element 12 and is free to move in a slot (not shown) through support element 12 as the shaft 77 moves in a general axial direction as will be explained in more detail below. Preferably, a tab 33 or other suitable mechanism is disposed on the opposite end of the extension arm 31 to allow a user to retract the shaft 77 and consequently the needle 26 following injection as will be explained in more detail below.

A trigger 64, which may be a button or other suitable device, is disposed on the exterior of the needle guide platform 18. Trigger 64 may be attached in a well-known manner to a first end 71 of a lever 66. Lever 66 is configured to pivot about a pin 70 or other suitable mechanism. A second end 72 of lever 66 preferably has a cam surface 73 and a flat or planar surface 74 which may be in substantial engagement with the plunger 29 when the needle 26 is in the retracted position as shown in FIG. 2a. Trigger 64 can activate release by other methods well-known in the art.

Reference will now be made to the operation of the apparatus 13 in order to more clearly describe the interrelationship among the elements as well as the overall injection cycle. Referring first to FIG. 2a, the apparatus 13 is shown generally in contactual relationship, via support surface 20, with a tissue 50 (enlarged in scale for clarity). The needle 26 is in the retracted position (i.e., not extending from aperture 24 of support surface 20). The medicament reservoir 44 is disposed in the proximal end of the channel 22. The second end 72 of lever 66, and more particularly, the planar surface 74, is in substantial engagement with the plunger 29 prohibiting axial movement thereof and holding the spring 35 in a compressed state. Furthermore, the piston 47 is disposed in the proximal end of housing 45.

After the apparatus 13 is in the desired location with regard to the tissue 50 and particularly that the support surface 20 is in substantial contactual relationship with and stabilized against the tissue 50, an operator may depress trigger 64 which will cause the needle 26, as will be described immediately hereinafter, to be advanced from the retracted position of FIG. 2a to an extended position as shown in FIG. 2b.

As the trigger 64 is depressed by the user, the lever 66 rotates about pin 70 which, causes the second end 72 of lever 66 to slidably disengage the plunger 29 of actuator 28. This, in turn, releases the compression spring 35 which causes the plunger 29 to move in a forward or distal axial direction. Compression spring 35 may alternately be any compression mechanism which will provide a force to drive plunger 29 in the forward axial direction. Plunger 29 contacts piston 47 and moves the medicament reservoir 44 in the axial direction along the proximal section 22a of channel 22 which correspondingly moves the attached needle 26 in the axial direction along the distal section 22b of channel 22. The forward axial movement of the needle 26 and the medicament reservoir 44 continues until the forward end of housing 45 contacts the forward wall portion 53 of channel 22. At this point the medicament reservoir 44 has moved a distance x (as shown in FIG. 2a) and the needle 26 has extended forwardly from the aperture 24 of the support surface 20 and into the tissue 50 by a corresponding penetration distance, x. It should be apparent that the penetration distance may be specifically chosen for various applications and corresponding changes to the dimensions of the elements, for example, but not limited to, the medicament reservoir 44 and the channel 22 could also be made to accommodate the chosen penetration distance. It should also be understood by one of ordinary skill in the art that the force required to axially move the medicament reservoir 44 and the needle 26 within the channel 22 is less than the force required to move the piston 47 which is sealingly disposed in housing 45 of the medicament reservoir 44.

As shown in FIG. 2c, the medicament reservoir 44 is in contact with the forward wall portion 53 of channel 22. Thus, forward axial movement of the needle 26 and the medicament reservoir 44 is impeded. Plunger 29, however, continues to move forward due to the extension of spring 35 and overcomes the resistive force of the sealingly disposed piston 47 in housing 45 of the medicament reservoir 44. As piston 47 moves in the forward axial direction it forces the volume of fluid or medicament 76 through the needle 26 and into the targeted site of injection within tissue 50.

Following injection of the fluid in the manner described above, the user normally may slide tab 33 in the proximal axial direction against the force of the spring which will in turn move the medicament reservoir 44 and the needle 26 in the corresponding direction. As plunger 29 axially slides in the proximal direction it contacts the cam surface 73 of the second end 72 of lever 66 causing the lever 66 to rotate about pin 70 in a counterclockwise position (in relation to FIGS. 2a–2c). At the same time, spring 35 is compressed by the plunger 29. As the plunger 29 moves past the second end 72 of lever 66, the lever 66 rotates in a general clockwise direction such that the planar surface 74 of lever 66 returns to substantial engagement with the plunger 29 as originally shown in FIG. 2a. Alternatively, the user may pull the needle 26 directly out of the tissue 50.

It should be understood by one skilled in the art that various actuator mechanisms may be employed in the invention. For example, the plunger 29 may alternatively be connected to a source of compressed gas with a valve which may be actuated by the trigger 64. Alternatively, the plunger 29 may be actuated by the user. Likewise, separate actuator assemblies could be employed in order to achieve extension of the needle 26 and movement of the fluid within the medicament reservoir 44 and through the needle 26 to the targeted site of injection.

Figure 3C:
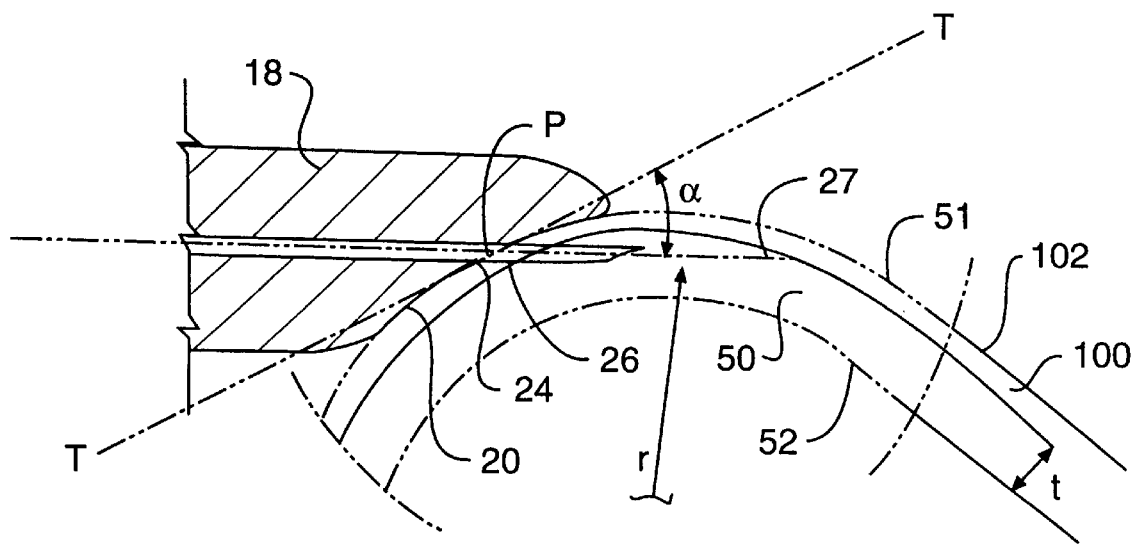
FIG. 3c is a detailed view of the relationship between the needle guide platform and exemplary multiple layers of tissue.
Figure 3A:
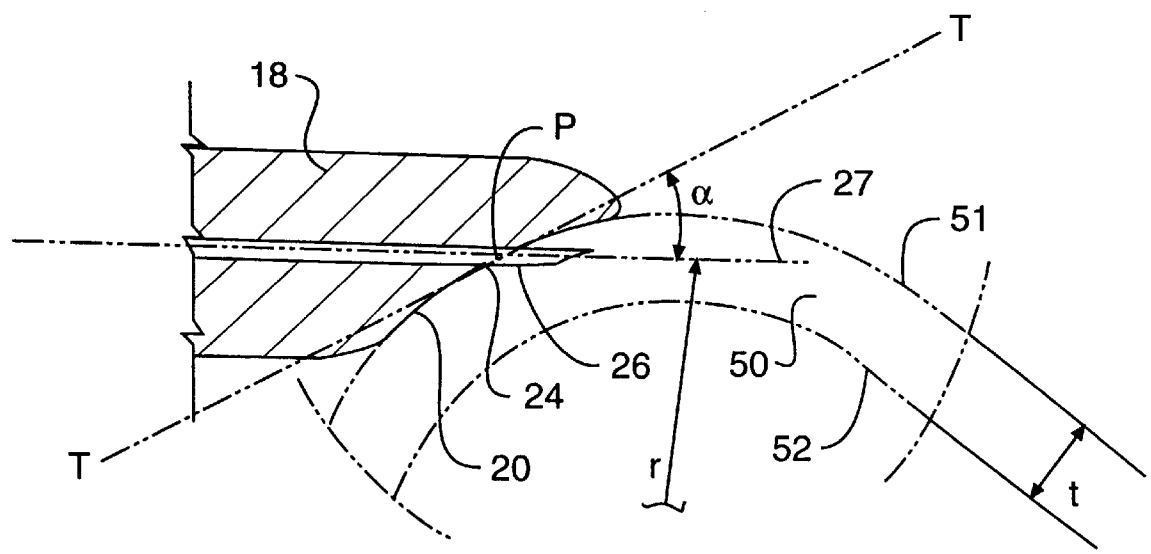
FIG. 3a is a detailed view of the relationship between the needle guide platform and an exemplary tissue.

Reference will now be made to FIG. 3a, where a detailed view of the support surface is shown in relationship to a representative tissue of the human body 50. As can be seen in FIG. 3a, and as described above, support surface 20 is configured to substantially contact the surface of the tissue 50. Tissue 50 includes an outer surface 51 and an inner surface 52. Outer surface 51 and inner surface 52, together define a tissue thickness, t, as shown in different scale to the needle guide platform portion 18 of apparatus 10 in FIG. 3a.

It should be understood by one of ordinary skill in the art that the apparatus 10 of the present invention has application to a wide variety of tissues 50, especially to thin layer tissues with configurations of varying radii of curvatures. Moreover, the spirit of the invention may also include flat tissues. Among the many biological tissues that the present invention is particularly suited to, but not limited to, are some layers of the walls of blood vessels and fallopian tubes, as well as the sclera of the eye.

Injections into tissue 50, especially of the thin layer tissue type, may be limited by the thickness t, defined by the outer surface 51 and the inner surface 52, as well as the radius of curvature r. The thickness t could range from about 0.3 mm to about 1.5 mm, in the case of the sclera of the human eye. The predominant limitation to such thin layer injections is the leakage which normally occurs along the needle 26 to the outer surface 51 due to insufficient penetration distance of the needle 26 into the thin tissue 50. Another limitation is the inability to stabilize the device against the targeted tissue 50, especially those tissues having small radii of curvature r, in order to provide a guided injection route and prevent errors due to human manipulation. In addition, tissue pliability or flexibility has presented numerous problems with regard to human control over the penetration distance of the needle and control over the overall placement of the needle in the targeted deposition site.

The exemplary embodiment, as shown in FIG. 3a and previously described above, overcomes these limitations. First, inserting the needle 26 at a penetration approach angle $\alpha$, which will be discussed in more detail below, allows the needle 26 to travel roughly parallel to the outer surface 51 of the tissue 50. The needle 26 is placed substantially between the outer surface 51 and the inner surface 52, and more particularly, preferably midway between the outer surface 51 and the inner surface 52. This positioning increases the penetration distance of the needle 26 into the tissue 50 sufficiently to reduce leakage and, for example, to at least greater than the tissue thickness t, as will be described in more detail below.

As can be seen in FIG. 3a, for an embodiment with a straight needle, the axis of injection 27 coincides with the longitudinal axis of the needle 26. The axis of injection 27 intersects the projection of support surface 20 across aperture 24. This intersection of the axis of injection 27 and the projection of support surface 20 across aperture 24 defines a point P. A tangent T—T may be defined at point P for the support surface 20 in a well known manner. Tangent T—T and the axis of injection 27, together, define the penetration approach angle $\alpha$. Angle $\alpha$ is measured in the plane defined by tangent T—T, the axis of injection 27 and a line drawn perpendicular to tangent T—T at point P. It should be apparent to one of ordinary skill in the art that support surface 20 may comprise varying shapes, for example, but not limited to, curved or planar, in order to substantially conform to the shape of the targeted tissue 50 when support surface 20 is brought into substantial contact with the outer surface 51 of tissue 50. Regardless of the shape of support surface 20, one may define tangent T—T at the intersection point P in the well-known manner. If support surface 20 is planar, then it should be understood that tangent T—T generally coincides with support surface and intersection point P may be defined at the intersection of the axis of injection 27 and the projection of support surface 20 across aperture 24.

Figure 3B:
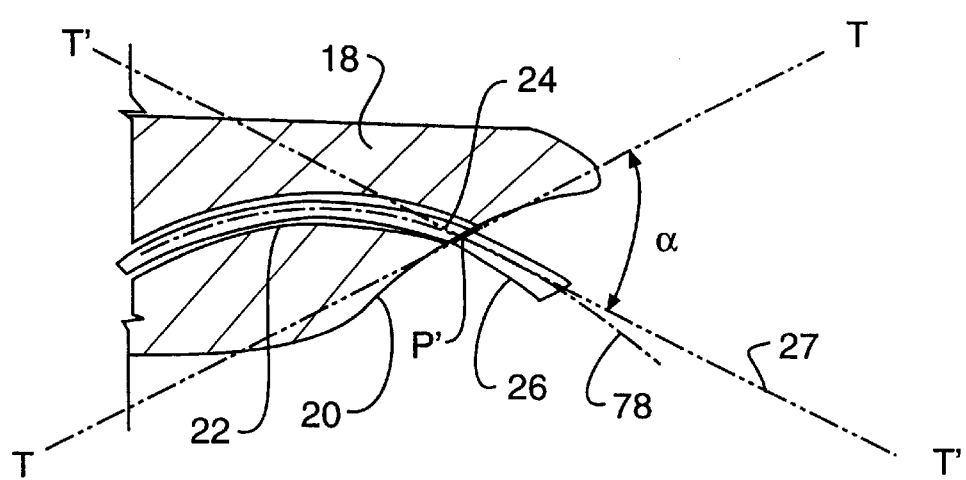
FIG. 3b illustrates an alternative embodiment for a curved needle.

Alternatively, it should be understood by one skilled in the art that the spirit of the invention may include a curved needle 26 disposed in a curved channel 22 for movement therethrough. An exemplary illustration of such an embodiment is shown in partial view in FIG. 3b. As can be seen in FIG. 3b, the longitudinal axis 78 of needle 26 is curved to preferably correspond to the curved axis of the curved channel 22. Needle 26 is movable along the curved longitudinal axis 78. The longitudinal axis 78 intersects the projection of support surface 20 across aperture 24. This intersection of the longitudinal axis 78 and the projection of support surface 20 across aperture 24 define a point P'. A tangent T—T may be defined at point P' for the support surface 20 in a well-known manner. Additionally, the axis of injection for a curved needle 26 may be defined as a second tangent T'—T' at point P' for the curved longitudinal axis 78 of needle 26. Together, tangent T—T and the axis of injection 27 (T'—T') define the penetration approach angle $\alpha$. Angle $\alpha$ is measured in the plane defined by tangent T—T and T'—T', the longitudinal axis 78 and a line drawn perpendicular to tangent T—T at point P'. It should be apparent to one of ordinary skill in the art that support surface may comprise varying shapes, for example, but not limited to, curved or planar, as described above.

As noted above and illustrated in FIGS. 1f, the invention may also be used if intervening layers of tissue 100 separate the apparatus 10 and the target tissue 50. FIG. 3c shows the needle guide platform 18 portion of apparatus 10 with a straight needle and used with multiple layers of tissue 100, 50. The penetration approach angle is determined as discussed above. Moreover, the alternate embodiments, including a curved needle shown in FIG. 3b, may also be used with intervening layers of tissue 100.

The minimum penetration distance of needle 26 that is needed to prevent leakage of a specific fluid or agent from a specific tissue may be estimated from the permeability and elastic properties of the particular tissue and the viscosity of the particular fluid or agent. The permeability of the tissue can be measured for porous media using relatively simple and well known experimental methods, such as those described in Fatt and Hedbys, Exp. Eye Res., Vol. 10, p. 243 (1970), the entirety of which is herein incorporated by reference.

For a desired imbedded penetration distance, there will be a range of penetration approach angles over which needle 26 may be inserted. The penetration approach angle $\alpha$ chosen for any specific application is governed by several factors. Among these are: the permeability of the particular tissue; the viscosity of the particular fluid or agent; the thickness t and radius of curvature r of the tissue 50; the size of the needle 26; and susceptibility to human error.

Generally, given all of the factors which can affect the penetration approach angle $\alpha$ for any specific application, a penetration approach angle $\alpha$ of up to about 60° is generally preferred. Such a range generally provides for a needle penetration distance at which leakage from the site of injection is minimized, if not eliminated, and potential for perforating the full width of the tissue (i.e., the inner surface) is eliminated. In addition, such a range virtually eliminates the variable of tissue pliability or flexibility and its effects upon control of needle placement within the tissue. Moreover, such a range provides application to a wide variety of tissue shapes, including nearly flat tissue surfaces.

Figure 4A:
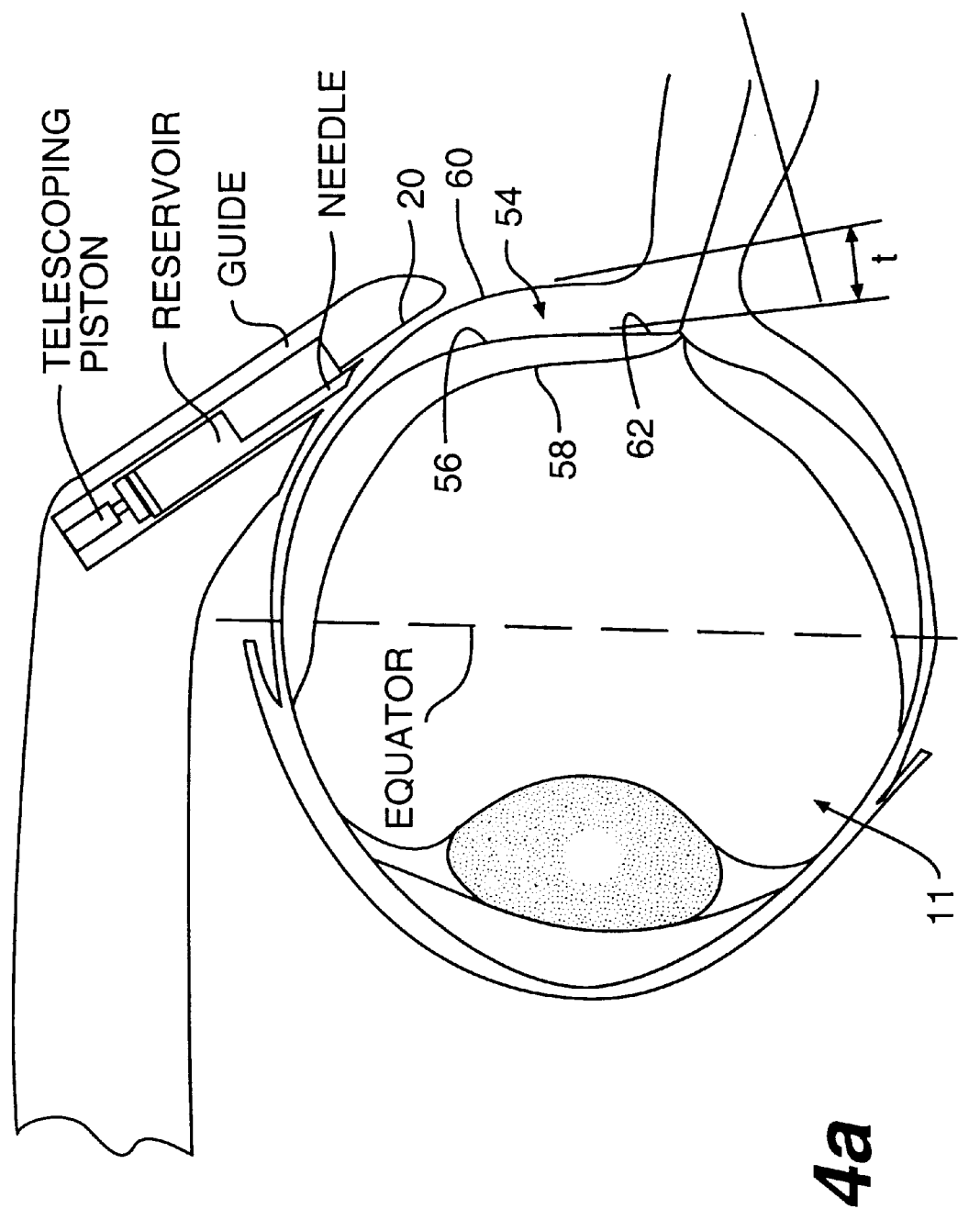
FIGS. 4a and 4b illustrate injection into the sclera region of the eye using an exemplary embodiment of the present invention.
Figure 4B:
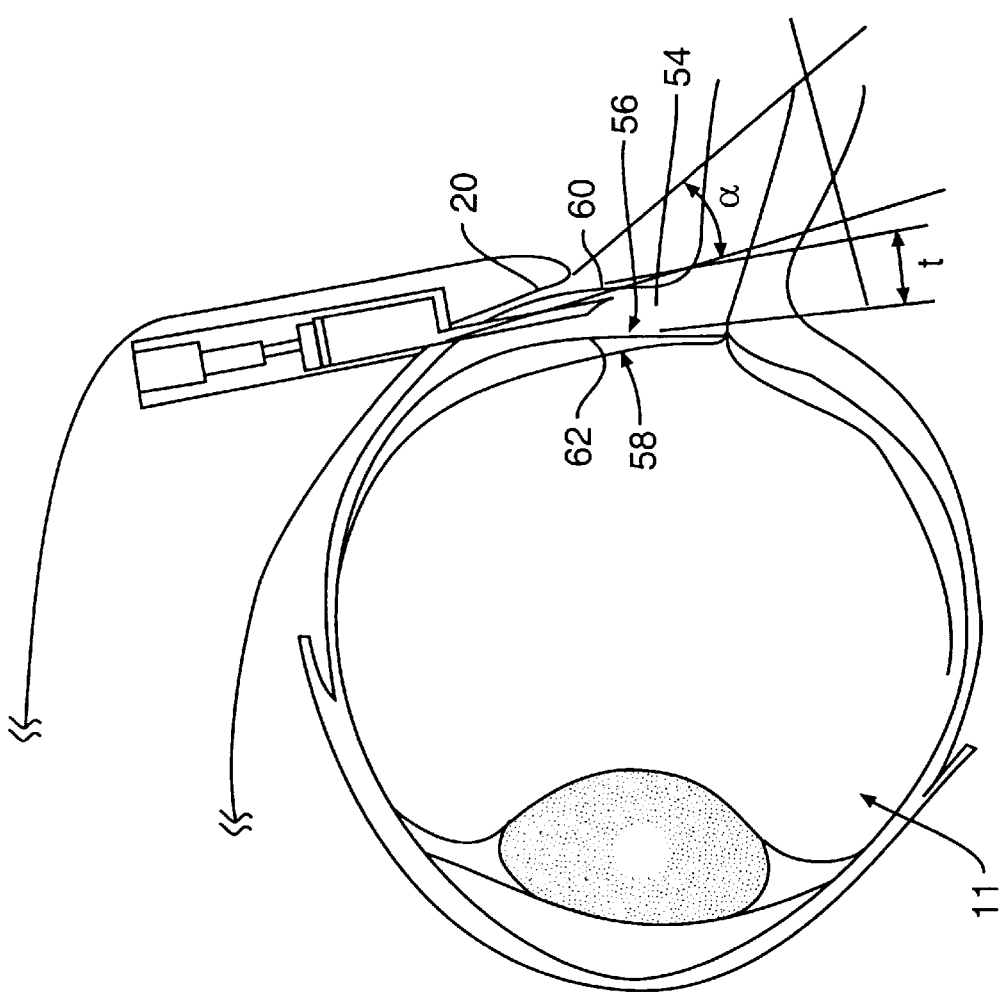

Referring to FIGS. 4a and 4b, an apparatus 10, shown in magnified detail view and similar to the exemplary embodiment illustrated in FIGS. 2a–2c, is shown in relationship to the sclera 54 of human eye. The sclera 54 of the human eye (shown not to scale in FIGS. 4a and 4b) has a thickness t ranging from about 0.3 mm near the equator of the eye to about 1.5 mm, defined by the outer surface 60 and inner surface 62. The sclera 54 covers the choroid 56 and the retina 58. As can be further seen in FIGS. 4a and 4b, support surface 20 is configured and shaped to conform to the outer surface 60 of the sclera 54 which is ultimately defined by the radius of curvature of the ocular globe or eye 11 of a typical human. Generally, the sclera 54 of the human eye has a radius of curvature of approximately 1.2 cm.

In order to imbed the needle 26 into the sclera 54 such that a sufficient hydrodynamic seal is formed between the needle 26 and the sclera 54 thereby minimizing leakage of the therapeutic fluid or agent, the penetration distance of the needle 26 may be approximately in the range of preferably about 1.5 mm to about 4 mm. More preferably, the penetration distance will be in the range of about 2 mm to about 3 mm. Given the radius of curvature and permeability of the sclera 54, the viscosity of the fluid or agent to be injected, and the targeted point of injection into and within the sclera 54, needle 26 may preferably be inserted at an approximate penetration approach angle α of about 30°. Taking into consideration the variability in the thickness of the sclera along the circumference of the eye, the appropriate placement of the fluid or agent into the sclera, and human operator error, a preferred range for the penetration approach angle α for injection into the sclera may be from about 20° to about 40°.

It may be necessary or desired to increase the penetration distance of needle 26 in order to provide, for example, but not limited to, more secure sealing or to inject at a particular position within the sclera 54. In order to accommodate such an increase in the penetration distance, a correlative change to the penetration approach angle may also be required.

Figure 6A:
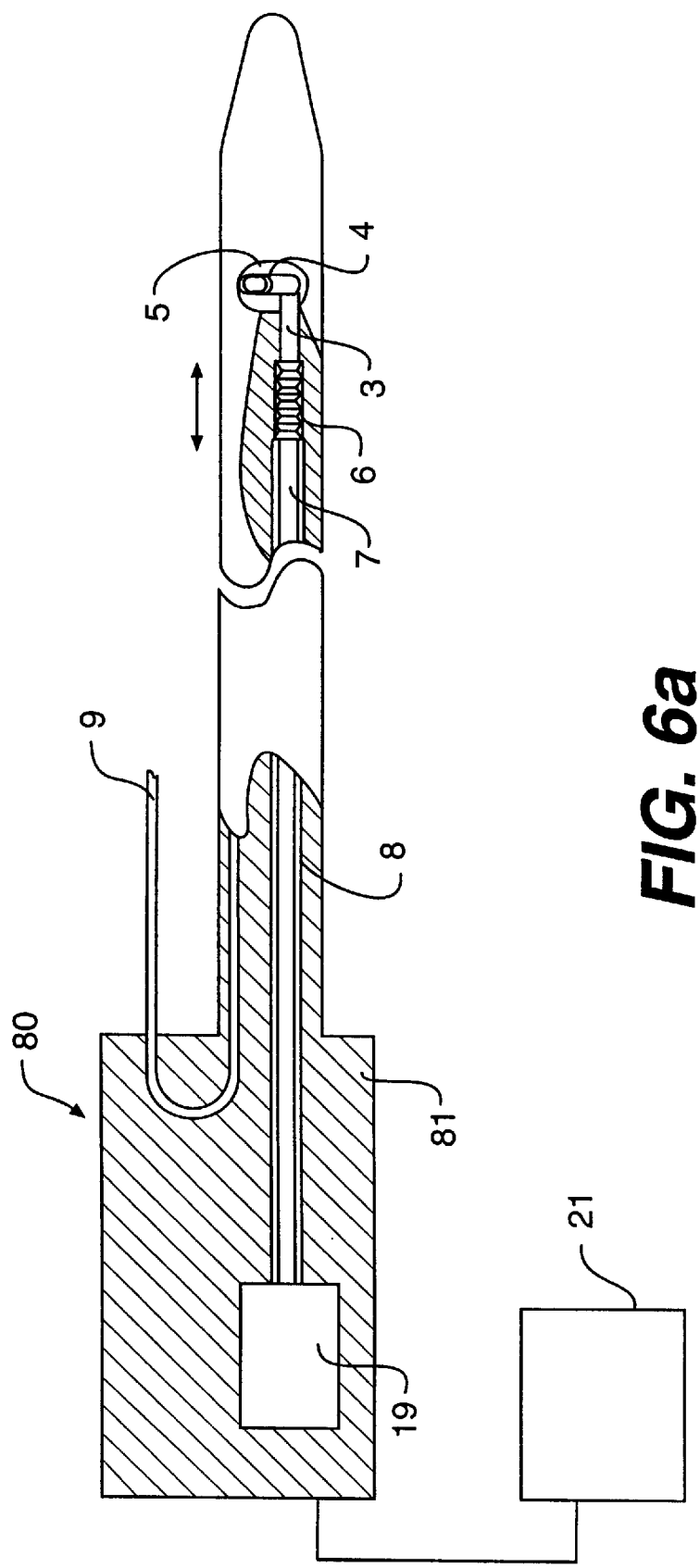
FIG. 6a is a sectional elevational view of a third exemplary embodiment of the present invention.
Figure 6C:
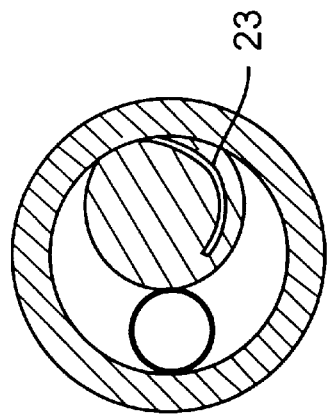
FIG. 6c is a sectional end view of the third exemplary embodiment of the invention shown with the needle retracted.
Figure 6D:
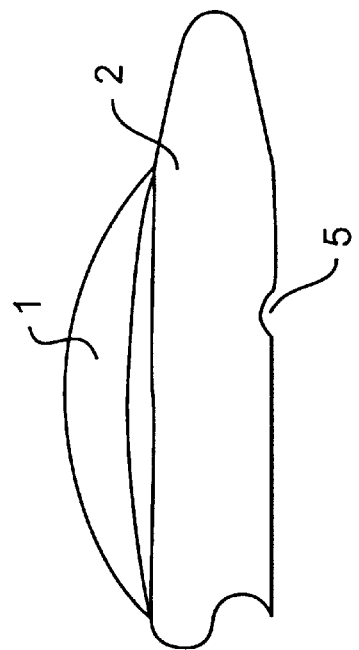
FIG. 6d is a partial detailed view of the contour of the support surface.
Figure 6B:
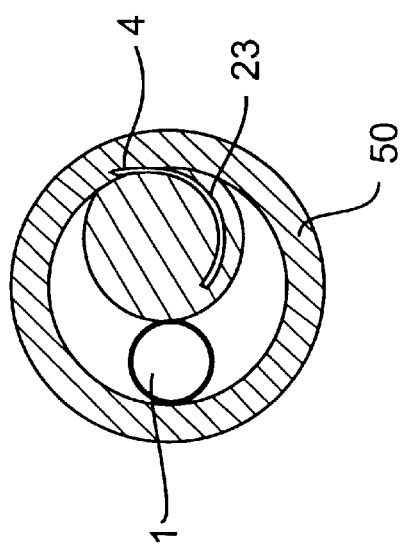
FIG. 6b is a sectional end view of the third exemplary embodiment of the invention shown with the needle extended.

Referring to FIGS. 6a–6c, a third exemplary embodiment of the present invention is shown. The third exemplary embodiment of the apparatus is represented generally by reference numeral 80. Apparatus 80 has a catheter body 81 with a guide channel 8 extending therethrough.

The catheter body 81 includes an external support surface 5 which is shaped to substantially conform to the surface of the tissue 50 into which the injection is to be made. An actuator 19 is disposed in the catheter body 81 and is connectable to a piston or plunger 7 for moving the plunger 7 along guide channel 8. It should be understood by one skilled in the art that actuator 19 may be manually or automatically operated, for instance by a controller 21 connected to actuator 19. It should also be understood by one skilled in the art that various actuator mechanisms may be employed in the invention. For example, the actuator 19 may be a gas/piston arrangement, a compression spring, or other suitable and practical device for moving piston 7 along guide channel 8.

A needle 4 or other suitable cannula device is disposed in the catheter body 81 in a curvilinear channel 23 (as shown in FIGS. 6b and 6c). Needle 4 is movable through channel 23 from a first retracted position to an extended position. The needle 4 may be advanced from the retracted position to the extended position by the actuator 19 and the piston 7 as will be described in more detail below. Needle 4 may be either preformed into a curvilinear shape, flexible, or a combination of the two.

Needle 4 preferably is connected at its proximal end to, and is in fluid flow communication with, a conduit 3. The conduit 3 is likewise preferably attached at its proximal end to a collapsible medicament reservoir 6. Collapsible reservoir 6 is preferably made of an elastic, bellows-like material such as rubber or plastic. Alternatively, it should be apparent to one of ordinary skill in the art that the needle 4 may be connected to a remote medicament reservoir through an extended conduit such as flexible tubing or other suitable mechanism.

As shown in FIG. 6d, a balloon 1, or other expansion member, is preferably disposed on the catheter body 81. According to the particular application of the apparatus, a balloon 1 may or may not be required. Balloon 1 is in fluid flow communication with an inflation conduit 9 for receiving an inflation fluid from a fluid source (not shown).

Reference will now be made to the operation of the apparatus 80, specifically as shown in FIGS. 6a–6d, in order to more clearly describe the interrelationship among the individual elements as well as the overall injection cycle.

The apparatus 80 and more particularly the catheter body 81 is introduced into the lumen of a vessel, for example the fallopian tubes, in a well known manner. The external support surface 5 is brought into close proximity with the targeted site of injection into tissue 50. Once the catheter 81 is in the desired location, the fluid source may be activated by the user which causes an amount of fluid to flow through inflation conduit 9 and thereafter to balloon 1. Balloon 1 expands in response to the fluid and acts to move the support surface 5 into substantial contactual relationship to the tissue 50 thereby conforming the tissue 50 to the contour of support surface 5.

Once the tissue 50 is conformed to the contour of support surface 5, an operator may activate the actuator 19 which in turn moves the plunger or piston 7 along the guide channel 8. This causes the needle 4 to move along the curvilinear channel 23 a preset distance such that the needle 4 may be imbedded into the tissue 50 at the desired penetration distance. Subsequent displacement of the plunger or piston 7 deforms the reservoir 6 causing fluid contained therein to be displaced through needle 4 and into the tissue 50.

Following injection of the fluid in the manner described above, the needle 4 may be retracted by reversing the above-described process and the catheter body 81 removed from the lumen of the vessel. Alternatively, it should be understood by one skilled in the art that multiple injections may be made.

Figure 7:
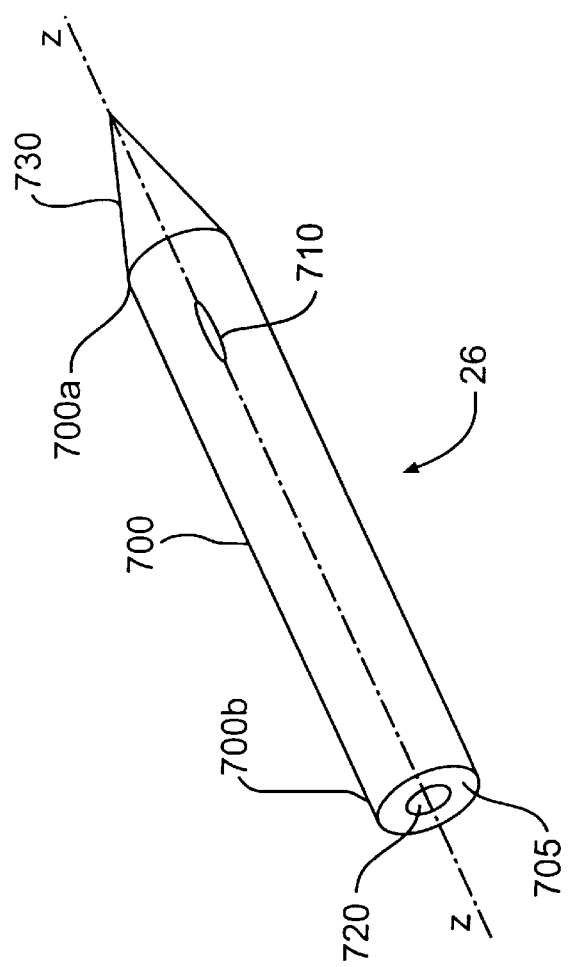
FIG. 7 is a detailed view of a fourth exemplary embodiment of the present invention.

An alternative embodiment of the present invention is shown in FIG. 7. As shown, needle 26 preferably comprises a single needle section 700 having a first end 700a and a second end 700b. Needle section 700 additionally includes a sidewall 705. Sidewall 705 defines an outlet 710 in needle 26. In a preferred embodiment, sidewall 705 defines outlet 710 near or adjacent first end 700a of needle 26. It should be apparent to one of ordinary skill in the art, that outlet 710 may be defined at a plurality of locations along needle 26. An inlet 720 is also disposed in needle 26. Inlet 720 can likewise be disposed near or adjacent second end 700b in needle 26. As noted above, inlet 720 can be formed in sidewall 705. However, it is preferred that inlet 720 be formed in the end of first end 700a, as shown in FIG. 7. It is also preferred that inlet 720 be in a substantial co-linear relationship with a longitudinal axis Z—Z of the lumen, or hollow space extending through needle 26 as shown in FIG. 7. In the present exemplary embodiment, it is preferred that needle 26 be used as part of the injection apparatus described above, but it should be understood by one of ordinary skill in the art that it is not limited to such use.

Needle 26 also preferably includes a sharpened point or tip 730 preferably disposed on first end 700a. It should be apparent to one of ordinary skill in the art that sharpened point 730 can be formed integral with needle 26 in a well-known manner or can be attached to needle 26 using any well-known technique. It should also be apparent to one of ordinary skill in the art that sharpened point 730 can comprise any number of shapes, including, but not limited to triangular or conical, as shown in FIG. 7.

As also shown in FIG. 7, it is preferred that outlet 710 be in a substantial non co-linear relationship with inlet 720 to allow an agent to be directed towards one surface of a targeted tissue as will be described in more detail below. It should be apparent to one of ordinary skill in the art that outlet 710 could be arranged in a plurality of configurations on needle 26 to accommodate the preferred non co-linear relationship, including but not limited to, for example, defining outlet 710 on an angled surface of sharpened point 730. In addition, it should be understood by one having ordinary skill in the art that a plurality of outlets 710 could be defined by sidewall 705 and that the plurality of outlets 710 could be configured in a plurality of arrangements, including, but not limited to, linearly along needle 26 or in an angular relationship around the circumference of needle 26.

Figure 8:
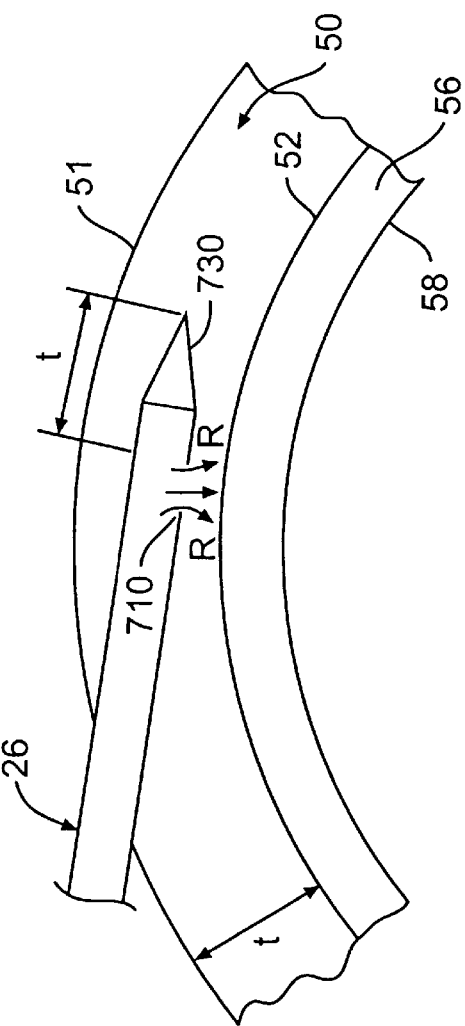
FIG. 8 illustrates injection into a tissue using the fourth exemplary embodiment of the present invention.

Turning now to FIG. 8, needle 26 is shown imbedded in a tissue 50, such as the sclera of the eye. Tissue 50 includes a first surface 51 and a second surface 52. As noted above, a plurality of tissues can be adjacent tissue 50. Exemplary tissues can include, but are not limited to, a choroid 56 and retina 58 of the eye. As described above, needle 26 is preferably imbedded into tissue 50 at a penetration approach angle that allows a penetration distance into tissue 50 which is sufficient to minimize leakage of the agent. As noted above, needle 26 is preferably imbedded into tissue 50 to at least greater than the tissue thickness, t.

In general, three basic factors influence the effectiveness of indirect injection. These factors include: the direction of agent flow (depicted as arrows R) from needle 26 in relation to a targeted surface of tissue 50, which is surface 52 in FIG. 8; the distance of outlet 710 from surface 52; and the velocity of the agent as it leaves needle 26 through outlet 710. It has been found that the exemplary embodiment shown in FIGS. 7 and 8, is extremely effective for accomplishing indirect injection of an agent to an underlying tissue, such as the retina 58 of the eye.

Indeed, as shown in FIG. 8, when injecting into the choroid 56 or retina 58 from tissue 50, such as the sclera, outlet 710 is preferably placed as close as possible and in a substantial orientation towards the targeted surface 52. The closer outlet 710 is located to surface 52, the greater the efficiency of the injection process. In other words, the closer outlet 710 is to surface 52, the greater the fraction of the total delivered agent that reaches the targeted tissue, for example, the choroid 56 or retina 58. Moreover, the geometry of outlet 710 also plays an important role in the efficiency of the injection. Generally, the smaller the outlet 710 is, the greater the agent velocity will be for a fixed volumetric flow rate.

Examples using the exemplary embodiments described above are provided herein below. It should be understood by one having skill in the art that the following examples serve to illustrate the present invention and should not be considered to limit the scope of the present invention.

EXAMPLE 1

A 33-gauge needle having an orifice of 100 microns was placed in the scleral tissue of the eye at a depth of greater than about the scleral thickness with the outlet of the needle oriented towards the inside surface of the sclera. An injection of 10 microliters of a 1% fluorescein dye solution at a rate of about 1 to 4 microliters/second, and using the technique described above produced, immediate staining of the retinal tissue. This staining occurred without the sharpened point of the needle penetrating through the sclera. The time required for staining of the retinal region was less than had previously been observed from staining resulting from diffusion of the fluorescein from the site of injection. In addition, when subsequent trials were performed with the outlet of the needle oriented towards the external surface (i.e., the surface opposite the choroid and retina) of the sclera, no immediate staining was observed. Therefore, it was concluded that the fluorescein dye solution was being delivered by convection from the outlet of the needle directly to the retina.

EXAMPLE 2

In another experiment, a 33-gauge needle having a 100 micron orifice was used to deliver large agents, for example, collodial carbon and virus particles, both of which are particulate suspensions in the range of 50 to 150 nanometers in diameter, directly to tissues underlying the sclera, such as the retina, without fully penetrating the sclera. Delivery of the collodial carbon particles was at a rate of about 1 to 4 microliters/second. Delivery of the virus particles was carried out at a rate of about 4 microliters/second. Previous experiments revealed that agents such as these tend to diffuse very slowly from the site of injection due to their large size. However, in the case of this experiment, the agents were found in the underlying tissues much earlier than could be explained by diffusion through the sclera.

EXAMPLE 3

A 33-gauge needle having a 100 micron orifice was placed in the scleral tissue of the eye at a depth of greater than about the scleral thickness with the outlet of the needle oriented towards the inside surface of the sclera. An adenovirus vector containing the gene for green fluorescent protein (GFP) was injected at a rate of about 4 microliters/second at a multiplicity of infection of 0.6. Delivery of the viral vector was verified by demonstrating that the cells of the choroid and retina expressed the GFP. Such expression within the choroid or retina cannot be accomplished without being transected by the virus.

CONCLUSION

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

We claim:

1. A method for injecting an agent into scleral tissue, the tissue having a first surface and a second surface defining a tissue thickness, said method comprising:

disposing a needle in an injection apparatus, the apparatus including a support element, a needle guide platform disposed on said support element and having an external support surface configured substantially similar to the natural curvature of the intact sclera, the support surface being configured to substantially conform to the geometry of one of the first and second surface of the tissue, and a channel therethrough, the needle movable along an axis of injection through the channel, the needle having a first end and a second end and including a sidewall defining an outlet in the needle and an inlet disposed in the needle, the inlet being in fluid flow communication with the outlet;

placing the needle in fluid flow communication with a medicament reservoir;

positioning the injection apparatus adjacent a tissue surface;

advancing the needle outwardly through the channel;

imbedding the needle into the scleral tissue at a penetration distance of greater than about the tissue thickness and such that the outlet is adjacent to, and oriented in a direction substantially facing, one of the first and second surfaces of the tissue; and transferring the agent into the tissue.

2. A method according to claim 1, wherein the needle is imbedded into the target tissue at a penetration distance of greater than about the target tissue thickness.

3. A method according to claim 2, wherein even if the needle were extended, it could not intersect the second target tissue surface.

4. A method according to claim 2, wherein the needle is imbedded into the target tissue at a penetration distance of about 1.5 mm to about 4 mm.

5. A method according to claim 2, wherein the needle is imbedded into the target tissue at a penetration distance of about 2 mm to about 3 mm.

6. A method according to claim 1, wherein in the transferring step, the agent is transferred at a rate of about 1 to about 10 microliters/second.

7. A method according to claim 6, wherein in the transferring step, the agent is transferred at a rate of about 1 to about 4 microliters/second.

8. A method according to claim 7, wherein in the transferring step, the agent is transferred at a rate of about 4 microliters/second.

* * * * *